US010455832B1

(12) United States Patent
Olson et al.

(10) Patent No.: US 10,455,832 B1
(45) Date of Patent: Oct. 29, 2019

(54) COMPOSITIONS AND METHODS OF PRODUCT APPLICATION TO TARGET AND KILL ALL LIFE STAGES OF BED BUGS

(75) Inventors: Joelle Francine Olson, Shoreview, MN (US); Larry Mitchell Lark, St. Paul, MN (US); Staci Jo Johnson, Burnsville, MN (US); Erin Fransen Loosbrock, Eagan, MN (US); William Jeffery Pattison, St. Paul, MN (US)

(73) Assignee: Ecolab USA Inc., St. Paul, MN (US)

( * ) Notice: Subject to any disclaimer, the term of this patent is extended or adjusted under 35 U.S.C. 154(b) by 87 days.

(21) Appl. No.: 13/278,024

(22) Filed: Oct. 20, 2011

Related U.S. Application Data

(60) Provisional application No. 61/406,891, filed on Oct. 26, 2010.

(51) Int. Cl.
| | |
|---|---|
| *A01N 25/12* | (2006.01) |
| *A01N 25/32* | (2006.01) |
| *A47B 57/08* | (2006.01) |
| *A61K 31/07* | (2006.01) |
| *A61K 31/14* | (2006.01) |
| *A61K 31/19* | (2006.01) |
| *A61K 31/51* | (2006.01) |
| *A61K 33/06* | (2006.01) |
| *A61K 33/18* | (2006.01) |
| *A61K 36/28* | (2006.01) |
| *A61K 39/00* | (2006.01) |
| *A61K 31/122* | (2006.01) |
| *A61K 31/194* | (2006.01) |
| *A01N 43/00* | (2006.01) |
| *A01N 43/46* | (2006.01) |
| *A61K 31/55* | (2006.01) |
| *A01N 37/08* | (2006.01) |
| *A61K 31/197* | (2006.01) |
| *A61K 31/355* | (2006.01) |
| *A61K 31/375* | (2006.01) |
| *A61K 31/455* | (2006.01) |
| *A61K 31/519* | (2006.01) |
| *A61K 31/525* | (2006.01) |
| *A61K 31/555* | (2006.01) |
| *A61K 31/593* | (2006.01) |
| *A61K 31/714* | (2006.01) |
| *A61K 31/4415* | (2006.01) |

(52) U.S. Cl.
CPC .................. *A01N 37/08* (2013.01)

(58) Field of Classification Search
USPC ....................................... 514/725
See application file for complete search history.

(56) References Cited

U.S. PATENT DOCUMENTS

| | | |
|---|---|---|
| 1,259,911 A | 3/1918 | Seibert |
| 3,304,646 A | 2/1967 | Staley |
| 3,484,374 A | 12/1969 | Henryk |
| 3,747,260 A | 7/1973 | Lovness |
| 4,217,722 A | 8/1980 | McMullen |
| 4,709,504 A | 12/1987 | Andric |
| 4,800,671 A | 1/1989 | Olson et al. |
| 4,862,638 A | 9/1989 | Stevenson |
| 5,102,662 A | 4/1992 | Gallagher |
| 5,119,586 A | 6/1992 | Townsend |
| 5,438,792 A | 8/1995 | Monett et al. |
| 5,454,186 A | 10/1995 | Gang |
| 5,597,599 A | 1/1997 | Smith et al. |
| 6,063,418 A | 5/2000 | Sugimoto et al. |
| 6,106,821 A | 8/2000 | Baker |
| 6,696,424 B1 | 2/2004 | Wheeler |
| 6,766,612 B1 | 7/2004 | Liu |
| 6,814,956 B2 | 11/2004 | Besser et al. |
| 7,444,711 B2 * | 11/2008 | Garcia et al. .................. 15/324 |
| 7,910,056 B2 | 3/2011 | Ivanine et al. |
| 8,146,290 B1 | 4/2012 | Telly |
| 8,282,952 B2 | 10/2012 | Smit |
| 8,413,370 B2 | 4/2013 | Messian |
| 8,661,728 B2 | 3/2014 | Borth |
| 8,789,309 B2 | 7/2014 | Fabry |
| 8,808,721 B2 | 8/2014 | Banfield |
| 8,931,206 B2 | 1/2015 | Olson et al. |
| 8,966,812 B2 | 3/2015 | McKnight |
| 9,125,392 B2 | 9/2015 | Olson et al. |
| 9,901,088 B2 | 2/2018 | Backmark et al. |
| 10,123,534 B2 | 11/2018 | Olson et al. |
| 10,136,631 B2 | 11/2018 | Thuis et al. |
| 2003/0033965 A1 | 2/2003 | Van Lint |
| 2004/0216367 A1 | 11/2004 | Klein |
| 2005/0138858 A1 | 6/2005 | Lyng |
| 2006/0086038 A1 | 4/2006 | Mosher |

(Continued)

FOREIGN PATENT DOCUMENTS

| | | |
|---|---|---|
| CA | 2130375 | 4/1995 |
| CN | 202026723 | 11/2011 |

(Continued)

OTHER PUBLICATIONS

Gangloff-Kaufmann, J.C. et al. 2006 Bed bugs in America: a pest management industry survey. Am. Entomol. 52: 105-106.*
Pest Management Professional, *The Business of Bed Bugs*, Michael F. Potter, Jan. 1, 2008 (8 pages).
www.bed-bug.net, Bed Bug Killer/How to Kill Bed Bugs/Bed Bug Information, printed Apr. 13, 2010 (1 page).
Bayer Environmental Science, Need to Know, *Temprid® SC now labeled for Bed Bugs*, vol. 7, No. 1, Feb. 18, 2010.
Penn State University, Dept of Entomology, Entomological Notes, Bed Bugs, http://ento.psu.edu/extension/factsheets/bedbugs, printed Apr. 13, 2010 (4 pages).
MGK® Product Code 027911, Material Safety Data Sheet, Bedlam™ Insecticide, Feb. 28, 2006 (2 pages).

(Continued)

*Primary Examiner* — Layla Soroush
(74) *Attorney, Agent, or Firm* — Merchant & Gould P.C.

(57) ABSTRACT

The present disclosure generally relates to the field of pest elimination including all life stages of bed bugs. The present disclosure includes compositions and methods of product application to target and kill all life stages of bed bugs.

17 Claims, No Drawings

(56) References Cited

U.S. PATENT DOCUMENTS

| | | |
|---|---|---|
| 2006/0283076 A1 | 12/2006 | Chambers et al. |
| 2007/0044372 A1 | 3/2007 | Lang et al. |
| 2007/0254907 A1 | 11/2007 | Bowles |
| 2008/0052982 A1 | 3/2008 | Windsor |
| 2008/0115406 A1 | 5/2008 | Duston et al. |
| 2008/0269177 A1 | 10/2008 | Bessette |
| 2008/0319029 A1 | 12/2008 | Richman et al. |
| 2009/0145019 A1 | 6/2009 | Nolen et al. |
| 2009/0145020 A1 | 6/2009 | McKnight |
| 2009/0223115 A1 | 9/2009 | Lang et al. |
| 2009/0313883 A1 | 12/2009 | Olson et al. |
| 2010/0011655 A1 | 1/2010 | Frisch |
| 2010/0212213 A1 | 8/2010 | Hope, III et al. |
| 2011/0072712 A1 | 3/2011 | Black et al. |
| 2011/0105333 A1 | 5/2011 | Israels |
| 2011/0113674 A1 | 5/2011 | Levy |
| 2011/0203159 A1 | 8/2011 | McKnight |
| 2011/0289822 A1 | 12/2011 | Duehl et al. |
| 2012/0012046 A1 | 1/2012 | Cain |
| 2012/0110894 A1 | 5/2012 | Black |
| 2012/0186137 A1 | 7/2012 | Schneidmiller et al. |
| 2012/0192479 A1 | 8/2012 | Schmitz |
| 2012/0210628 A1 | 8/2012 | Park et al. |
| 2012/0233907 A1 | 9/2012 | Pattison et al. |
| 2012/0240451 A1 | 9/2012 | Ricks |
| 2012/0285076 A1 | 11/2012 | Banfield |
| 2012/0301532 A1 | 11/2012 | Carey et al. |
| 2013/0031825 A1 | 2/2013 | Dass |
| 2013/0067796 A1 | 3/2013 | Dong et al. |
| 2013/0180161 A1 | 7/2013 | Vasudeva |
| 2013/0184153 A1 | 7/2013 | Dieleman |
| 2013/0232849 A1 | 9/2013 | Schumacher |
| 2013/0291427 A1 | 11/2013 | Prohaska |
| 2013/0312313 A1 | 11/2013 | Lefkowitz et al. |
| 2014/0020278 A1 | 1/2014 | Smith |
| 2014/0020280 A1 | 1/2014 | Cullen |
| 2014/0033597 A1 | 2/2014 | Vasudeva et al. |
| 2014/0041284 A1 | 2/2014 | Nugent |
| 2014/0187425 A1 | 7/2014 | Allen |
| 2014/0216367 A1 | 8/2014 | Norman et al. |
| 2014/0290123 A1 | 10/2014 | Duff |
| 2014/0311016 A1 | 10/2014 | Wang |
| 2015/0007485 A1 | 1/2015 | Hortel et al. |
| 2016/0316750 A1 | 11/2016 | Gries et al. |
| 2017/0251655 A2 | 9/2017 | Frutos et al. |
| 2019/0098886 A1 | 4/2019 | Thuis et al. |
| 2019/0098898 A1 | 4/2019 | Olson et al. |

FOREIGN PATENT DOCUMENTS

| | | |
|---|---|---|
| EP | 0416255 | 3/1991 |
| KR | 20080036963 | 4/2008 |
| KR | 20100092641 | 8/2010 |
| KR | 20130122739 | 11/2013 |
| WO | WO97/24034 | 7/1997 |
| WO | WO 2005070209 A1 * | 8/2005 |
| WO | 2008/030385 A2 | 3/2008 |
| WO | WO2009/047584 A1 | 4/2009 |
| WO | WO2009/075839 | 6/2009 |
| WO | WO2012/162703 | 11/2012 |
| WO | WO2013115719 | 8/2013 |
| WO | WO2014/028835 | 2/2014 |
| WO | WO2015/089661 | 6/2015 |

OTHER PUBLICATIONS

TARR Status Report, http://tarr.uspto.gov/, U.S. Appl. No. 77/771,410, Registration No. 3751703, mark:Bedlam Insecticide, printed Apr. 12, 2010 (2 pages).

FMC Corporation, *Best Management Practices*, Bed Bugs, 2009 (3 pages).

Snell, Eric J., Smith, Todd, Sexton, Wally, *Eclosion of Bed Bug (Cimex Lectularius) Eggs after Exposure to Various Compounds*, Snell Scientifics LLC, Meansville, GA, submitted paper at the National Conference on Urban Entomology in Tulsa, OK, May 18-21, 2008 (1 page).

Barcay, S.J. and Olson, J.F., *From Detection through Protection: Solutions for Fighting Bed Bug Infestations*, 13 pgs. (2010).

Adler et al., Modified Atmospheres. In: Alternatives to pesticides in stored-product IPM, (edited by Subramanyam and Hagstrum), Kluwer Academic Publishers, Boston, pp. 105-146 (2000).

Anderson, J.F. et al., A carbon dioxide, heat and chemical lure trap for the bedbug, Cimex lectularius, Medical and Veterinary Entomology, vol. 23, pp. 99-105 (2009).

Cardinal Professional Products, ECO2FUME®, http://www.cardinalproproducts.com/eco2fume.htm, 2 pages, printed Mar. 30, 2011.

Continental Carbonic, Use Dry Ice to Remove Bed Bugs, http://www.continentalcarbonic.com/dryice/remove-bed-bugs-dry-ice.php, 1 page, printed Sep. 20, 2010.

Gries et al., Bed Bug Aggregation Pheromone Finaly Identified, Angewandte Chemie International Edition, Dec. 21, 2014, 5 pages.

Gries et al., Supporting Information Bed Bug Aggregation Pheromone Finaly Identified, Angewandte Chemie International Edition, Dec. 21, 2014, 24 pages.

International Search Report and Written Opinion for PCT/IB2012/052756 dated Jan. 29, 2013.

International Search Report and Written Opinion for PCT/US2015/017115 dated Jun. 1, 2015.

Luckow, Scientists Developing Pheromone-Laced Bed Bug Trap, Pest Control Technology, Jun. 2015, 2 pages.

Stern Environmental Group, Bed Bug Control Services for Hotels, Motels, and Apartment Buildings; http://www.sternenvironmental.com/bedbugs/commercial.php, 3 pages, printed Sep. 20, 2010.

Supplementary European Search Report (EP 12 79 6003) dated Feb. 5, 2015 (8 pages).

Tvedten, Steve, The Bug Stops Here, http://www.getipm.com/thebestcontrol/bugstop/control_bed_bugs.htm, 2 pages, printed Sep. 20, 2010.

National Center for Healthy Housing, What's Working for Bed Bug Control in Multifamily Housing: Reconciling best practices with research and the realities of implementation, before Oct. 20, 2011.

International Search Report and Written Opinion for International Application No. PCT/US2015/034715, dated Sep. 1, 2015, 15 pages.

Extended European Search Report for Aplication No. 15751451.4 dated Dec. 4, 2017.

Extended European Search Report for Application No. 15809461.5 dated Oct. 19, 2017.

D.C. Robacker, "Attraction of both sexes of Mexican fruit fly, Anastrepha ludens, to a mixture of ammonia, methylamine, and putrescine," Journal of Chemical Ecology, vol. 19, No. 12, (1993).

Extended European Search Report for Application No. 17158799.1 dated Sep. 7, 2017.

* cited by examiner

COMPOSITIONS AND METHODS OF PRODUCT APPLICATION TO TARGET AND KILL ALL LIFE STAGES OF BED BUGS

RELATED APPLICATIONS

This application claims priority to Provisional Application No. 61/406,891 filed on Oct. 26, 2010, which is incorporated by reference herein in its entirety.

FIELD

The present disclosure generally relates to the field of pest elimination including all life stages of bed bugs. The present disclosure includes compositions and methods of product application to target and kill all life stages of bed bugs.

BACKGROUND

Bed bugs are small insects that feed solely on the blood of animals. The common bed bug, *Cimex Lectularus*, is the species of bed bug that has most adapted to living with humans. Bed bugs have lived with humans since ancient times, although many people living in the United States have never seen a bed bug. However, the increase of international travel in recent decades has contributed to the resurgence of bed bugs in the United States. There are many aspects of bed bugs that make it difficult to eradicate them once they have established a presence in a location.

Adult bed bugs are about ¼ inch or about 6 millimeters long, 5-6 millimeters wide, and reddish-brown with oval, flattened bodies. The immature nymphs are similar in appearance to the adults but smaller and lighter in color. Bed bugs do not fly, but they can move very quickly over surfaces. Female bed bugs lay their eggs in secluded areas and can deposit up to five eggs per day, and as many as 500 during a lifetime. The bed bug eggs are very small, about the size of a dust spec. When first laid, the eggs are sticky causing them to adhere to surfaces.

Bed bugs can go long periods of time without feeding. Nymphs can survive months without feeding and the adults for more than a year. Infestations are therefore not likely to be eliminated by leaving a location unoccupied.

Bed bugs are active during the nighttime and primarily hide during the daytime into tiny crevices or cracks. Bed bugs may find easy hiding places in beds, bed frames, furniture, along baseboards, in carpeting, and countless other places. Bed bugs tend to congregate but do not build nests like some other insects.

Bed bugs obtain their sustenance by drawing blood through an elongated beak. They may feed on a human for 3 to 10 minutes although the person is not likely to feel the bite. After the bite, the victim often experiences an itchy welt or swelling in the area of the bite. However, some people do not have any reaction or only a very small reaction to a bed bug bite. Bed bug bites have symptoms that are similar to other insect bites, such as mosquitoes and ticks. It is not possible to determine whether the bite is from a bed bug or another type of insect without actually observing the bed bug. As a result, bed bug infestations may go long periods without being detected.

Bed bug infestations originate by a bed bug being carried into a new area. Bed bugs are able to cling to possessions and hide in small spaces so that they may easily be transported in a traveler's belongings. As a result, buildings where turnover of occupants is high, such as hotels or apartments, are especially vulnerable to bed bug infestations. Because of all the features of bed bugs described herein, bed bugs are difficult to eradicate. Professional pest removal specialists and pesticides are needed. Bed bug eggs are especially difficult to eradicate with 100% efficacy.

It is against this background that the present disclosure is made.

SUMMARY

Surprisingly, it has been found that certain compositions and methods of treatment are especially effective at treating all life stages of bed bugs, including bed bug eggs.

In some embodiments, the present disclosure relates to a pesticide composition consisting of acetamiprid, bifenthrin, and optional additional adjuvants where this composition is effective at eliminating 100% of bed bug eggs.

In some embodiments, the present disclosure relates to a method of treating or preventing bed bugs, where the method involves providing a first pesticide composition and then applying the first pesticide composition to a treatment area. Additional pesticide compositions can be used in variations of this embodiment.

In some embodiments, the present disclosure relates to a method of treating or preventing bed bugs where the method involves inspecting the surface of an article for the presence of bed bugs, applying a treatment such as an insecticide spray, an insecticide dust, and combinations thereof, encasing the article, and providing at least one additional treatment such as vacuuming the article, steaming the article, laundering the article, disposing of the article, applying a heat or cold treatment to the article, and sealing cracks and crevices on the article.

DETAILED DESCRIPTION

In some embodiments, the present disclosure relates to pesticide compositions that use acetamiprid, bifenthrin, or both, along with optional additional adjuvants. In some embodiments, the present disclosure relates to pesticide compositions that use a composition consisting of a combination of acetamiprid and bifenthrin, with optional additional adjuvants. Surprisingly, it has been found that this composition is effective at eliminating 100% of bed bug eggs, where other bed bug pesticides are not effective at eliminating 100% of bed bug eggs. In some embodiments, these compositions can be used as part of a method of targeting and killing all life stages of bed bugs.

Compositions

The pesticide compositions include acetamiprid, bifenthrin, or both, along with optional additional adjuvants. It has been found that a combination of acetamiprid and bifenthrin is effective at eliminating 100% of bed bug eggs where other bed bug pesticides do not have this level of efficacy. There are a number of commercially available bed bug pesticides and they are sold in a variety of physical forms and act through a variety of mechanisms. While not wanting to be bound by theory, it is believed that acetamiprid mimics an insect's neurotransmitters causing the nervous system to overstimulate, which ultimately leads to death. Bifenthrin is believed to prevent the sodium channels on insect neurons from closing, which leads to continual nerve impulse transmissions and ultimately death. And the combination of these two pesticides is effective at eliminating 100% of bed bug eggs. In contrast, some pesticides contain solvents and alcohols that eliminate bed bug eggs by dissolving the egg. Other pesticides work as a repellant. The pesticide compositions of the present disclosure do not work by dissolving the egg or by repelling bed bugs. Accordingly, in some embodiments, the present pesticide compositions can be free of solvent. In some embodiments, the present pesticide compositions can be free of alcohol. And in some embodiments, the present pesticide compositions are not repellants and can be directly applied to harborage areas. The disclosed pesticide compositions preferably contain, in the use solution, from about 0.001 to about 0.07 wt. %, or about 0.05 to about 0.07 wt. % of bifenthrin and about 0.005 to about 0.10 wt. %, or about 0.025 to about 0.05 wt. % of acetamiprid.

The disclosed pesticide compositions can optionally include additional adjuvants such as a carrier, surfactant, pheromone, food attractant, and the like. The disclosed pesticide compositions can be in a variety of physical forms including liquids, emulsions, structured liquids, thickened liquids, powders, wetted powders, suspended concentrates, microencapsulates, granules, solid blocks, and the like. In some embodiments, the pesticide composition is preferably a wetted powder. The disclosed pesticide compositions can be sold as a use solution or as a concentrate. In general, a concentrate refers to a composition that is intended to be diluted to provide a use solution that contacts an object to provide the desired effect. The pesticide compositions that contact the pests or surrounding areas can be referred to as the use compositions.

Methods of Use

In some embodiments, the present disclosure relates to methods of applying product to target and kill all life stages of bed bugs. In some embodiments, the present disclosure relates to a method of applying product as part of a treatment program. The disclosed compositions may be used as part of a method or treatment program.

In some embodiments, the present disclosure relates to a method of treating or preventing bed bugs. In this method, an article is inspected to determine if bed bugs are present or not. If bed bugs are present, a treatment or pesticide composition can be applied. The treatment or pesticide composition can include a dust, a contact agent, a flushing agent, a liquid residual pesticide, and combinations thereof. After treating the article, the article can be encased. For small articles such as pillows, bedding, clothing, window treatments, telephones, remote controls, alarm clocks, and the like encasing can involve placing the article in a bag and closing or sealing the bag. In an embodiment, soft articles like window treatments, towels, bedding, clothing, etc., can be isolated and treated using non-pesticide treatments, discarded, or laundered. For medium sized articles such as furniture, mattresses, box springs, headboards, nightstands, and the like, encasing can involve wrapping the article in plastic, placing the article in a larger bag, or putting a tent around the article. Finally, for really large articles, such as entire rooms, entire buildings, entire cars, buses, trains or airplanes, entire stores, and the like, encasing can involve sealing the room at the doors and/or vents with plastic, tenting the entire room or building, and the like. The method can also include providing another treatment such as vacuuming the article, steaming the article, laundering the article, disposing of the article, applying a heat or cold treatment to the article, spot treatment, or sealing cracks and crevices on the article.

Exemplary articles that are treated include a mattress, a boxspring, bedding, baseboards, headboards, nightstands, carpet, furniture, mirrors, pictures, light fixtures, carpet, window treatments, walls, ceilings, floors, clothing, appliances, commercial fixtures, telephones, remote controls, alarm clocks, cars, buses, trains, airplanes, and pet bedding.

The article can be located in a variety of places including a hotel, a house, an apartment or multi-family complex, restaurants, an office building, a movie theater, a train, a bus, an airplane, a car, a truck, a retail store, a college dormitory, a hospital, and a nursing home. When the article is located in a room, such as a hotel room, dormitory, hospital or nursing home room, or apartment, the adjacent rooms above, below, and on the sides may also be treated. When the article is located in a larger space such as a theater, restaurant, or retail store, the entire facility may be treated, or the locations where people are most likely to congregate can be treated.

In some embodiments, the present disclosure relates to a method of treatment that includes providing a first pesticide composition and applying the first pesticide composition to a treatment area. The first pesticide composition can be a dust, contact or flushing agent, or liquid residual pesticide or a combination of these. In some embodiments, the first pesticide composition is applied to a specific treatment area such as towels, bedding, window treatments, shower curtains, baseboards, headboards, nightstands, cracks, crevices, box springs, mattresses, nonvisible surfaces, electrical outlets, and electrical switch plates. In an alternative embodiment, soft articles, such as towels, bedding, window treatments, and shower curtains are not treated with pesticide, but rather are isolated and either discarded, treated using a non-pesticide treatment such as heat, or laundered. After the first pesticide composition is applied, an optional second pesticide composition can be applied. The second pesticide composition and the first pesticide composition can be the same or different pesticides. The second pesticide composition can be applied shortly after the first pesticide composition. Alternatively, the second pesticide composition can be applied hours, days, or weeks after the first pesticide composition. In some embodiments, the second pesticide composition can be a dust, contact or flushing agent, or liquid residual pesticide or a combination of these. In some embodiments, the second pesticide composition is applied to a specific treatment area such as cracks, crevices, baseboards, headboards, nightstands, mattresses, and box-springs. After the second pesticide composition is applied, an optional third composition can be applied. The third pesticide composition and the first or second pesticide compositions can be the same or different pesticides. The third pesticide composition can be applied shortly after the second pesticide composition. Alternatively, the third pesticide composition can be applied hours, days, or weeks after the second pesticide composition. In some embodiments, the third pesticide composition can be a dust, contact or flushing agent, or liquid residual pesticide or a combination of these. In some embodiments, the third pesticide composition is applied to a specific treatment area such as cracks, crevices, baseboards, headboards, nightstands, mattresses, and box-springs.

In an embodiment, a treatment area or article is treated with a pesticide at least twice. In an embodiment, a treatment area or article is treated with a pesticide at least three times. In an embodiment, the method uses a first, second, and third pesticide composition where the second pesticide composition is applied within 24 hours of the first pesticide composition, and the third pesticide composition is applied within two weeks of the first pesticide composition. In some embodiments, the method uses a first, second, and third pesticide composition where the pesticides are applied on a schedule that coincides with the bed bug life cycle. In some embodiments, the method also includes treating a treatment area or article with ultraviolet light. In some embodiments, the first pesticide is effective at eliminating 100% of bed bug eggs where there are zero hatched eggs two weeks after treatment. In some embodiments, the first pesticide, second pesticide, and/or third pesticide is a pesticide composition consisting of acetamiprid, bifenthrin, and optional additional adjuvants, and is effective at eliminating 100% of bed bug eggs where there are zero hatched eggs two weeks after treatment.

The present disclosure may be better understood with reference to the following examples. These examples are intended to be representative of specific embodiments of the disclosure, and are not intended as limiting the scope of the disclosure.

EXAMPLES

Example 1—Effect of Pesticide Dusts on Bed Bug Egg Mortality

This example determined the effect of various pesticide dusts on bed bug egg mortality. For this example, bed bug eggs were created in advance by placing ten adult male bed bugs and 10 adult female bed bugs in a 2-ounce jar for one week. The jar contained a two-sided egging sheet that the eggs were deposited on. After one week, the adult bed bugs were removed from the jar and the number of eggs on both sides of the egging sheet were counted and recorded. Twenty to thirty eggs were needed for each round of testing. The eggs were observed under a microscope for any signs of impending hatching and those were recorded.

Pesticide dust was mixed according to the label instructions. The egging sheet was placed on a 6×6 inch panel and 0.113 grams of pesticide dust was applied to the panel. The egging sheet was flipped to the other side and placed on the 6×6 inch panel, and another 0.113 grams of pesticide dust was applied to the panel. For a control, no treatment was applied or 0.113 grams of powdered sugar was applied. The treated egging sheet was then placed in a 2-ounce jar. The eggs were observed for hatching two weeks after exposure to the pesticide dust. Four replicates were completed and the results are recorded in Table 1 along with the names and vendors of the pesticide dust.

TABLE 1

Effect of Pesticide Dust on Bed Bug Egg Mortality

| Product | Vendor | Percent of Unhatched Eggs at 2 Weeks | | | |
| --- | --- | --- | --- | --- | --- |
| Delta Dust | Bayer | 35% | 4% | 65% | 35% |
| Tempo 1% | Bayer | 38% | 48% | 43% | 43% |
| Pyganic Dust | MGK | 64% | 24% | 49% | 46% |
| Drione | Bayer | 59% | 29% | 41% | 43% |
| Alpine | BASF | 0% | 47% | 0% | 16% |
| No Treatment | (control) | 23% | 5% | 0% | 9% |
| Powder Sugar | (control) | 8% | 7% | 0% | 5% |

Table 1 shows that no dust was 100% effective at eliminating bed bug eggs after two weeks.

Example 2—Effect of Pesticide Aerosols on Bed Bug Egg Mortality

Example 2 determined the effect of pesticide aerosols on bed bug egg mortality. For this example, bed bug eggs were prepared on an egging sheet as in Example 1. 0.95 grams of various pesticide aerosols was applied to both sides of the egging sheet using the 6×6 inch panel described in Example 1. The sprayed egging sheet was then placed in a 2-ounce jar. The eggs were observed for hatching two weeks after application of the aerosol. Three replicates were completed for each aerosol and the results were averaged and are recorded in Table 2 along with the names and vendors of the pesticide aerosol.

TABLE 2

Effect of Pesticide Aerosols on Bed Bug Egg Mortality

| Product | Vendor | Averaged Percent of Unhatched Eggs at 2 Weeks |
| --- | --- | --- |
| 565 Plus XLO | Whitemire Microgen | 10% |
| SSI50 | Chemtech | 14% |
| Pronto | MGK | 15% |
| Mother Earth | Whitemire Microgen | 25% |
| Bedlam | MGK | 15% |
| Good Night | Sprayaway | 25% |
| Rest Easy | JT Eaton | 40% |
| Sterifab | Noble Pine Products | 25% |
| Eco KO | EcoSmart | 10% |
| Water | (control) | 0% |

Table 2 shows that no aerosol was 100% effective at eliminating bed bug eggs after two weeks. It was observed that bed bug egg mortality was dependent on how far away the aerosol was from the 6×6 inch panel when the aerosol was applied. Products applied at a short range (i.e., <1 foot) had a more significant effect than products applied at greater than 2 feet away. This suggests that efficacy is likely due to the additives and solvents in the composition and not the active ingredients.

Example 3—Effect of Fogging Agents on Bed Bug Egg Mortality

Example 3 determined the effect of pesticide fogging agents on bed bug egg mortality. For this example, bed bug eggs were prepared on an egging sheet as in Example 1. Various pesticide fogging agents were applied to both sides of the egging sheet using an Actisol compact unit at a rate of 12 psi/second in an enclosed 2×2 foot space where the egging sheet was standing vertically in the enclosed space. For a control, no treatment or water was applied. The sprayed egging sheet was then placed in a 2-ounce jar. The eggs were observed for hatching two weeks after application of the pesticide. Three replicates were done for each product and the results were averaged. The results are recorded in Table 3 along with the names and vendors of the pesticide.

TABLE 3

Effect of Pesticide Fogging Agents on Bed Bug Egg Mortality

| Product | Vendor | Averaged Percent of Unhatched Eggs at 2 Weeks |
| --- | --- | --- |
| No Treatment | (control) | 9.5% |
| Water | (control) | 31.2% |
| Pyrocide 100 | MGK | 26.1% |
| Alto Cirrus | MGK | 18.9% |
| Cirrus | MGK | 48.8% |

Table 3 shows that the fogging agents were not effective at eliminating 100% of bed bug eggs two weeks after treatment.

Example 4—Effect of Liquid Residual Pesticide on Bed Bug Egg Mortality

Example 4 determined the effect of liquid residual pesticides on bed bug egg mortality. For this example, bed bug eggs were prepared on an egging sheet as in Example 1. 0.95 grams of liquid residual pesticides were mixed according to the instructions on the label and applied to the egging sheet as in Example 2. For a control, no treatment or water was applied. The treated egging sheet was then placed in a 2-ounce jar. The eggs were observed for hatching two weeks after application of the pesticide. Three replicates were done for each product and the results were averaged. The results are recorded in Table 4 along with the names of the pesticide.

TABLE 4

Effect of Liquid Residual Pesticides on Bed Bug Egg Mortality

| Product | Vendor | Averaged Percent of Unhatched Eggs at 2 Weeks |
| --- | --- | --- |
| Cykick | Whitmire Microgen | 62% |
| Temprid | Bayer | 90% |
| Transport GHP | FMC | 100% |
| Suspend | Bayer | 60% |
| Water | (control) | 20% |
| No Treatment | (control) | 10% |

Table 4 shows that only Transport, a combination of acetamiprid and bifenthrin, was effective at eliminating 100% of bed bug eggs because 100% of the eggs were unhatched two weeks after treatment.

The above specification, examples and data provide a complete description of the disclosed compositions and methods of use. Since many embodiments of the disclosure can be made without departing from the spirit and scope of the invention, the invention resides in the claims.

We claim:

1. A method of treating or preventing bed bugs, the method comprising:
   (a) applying a first pesticide composition to a treatment area, wherein the first pesticide composition comprises from about 0.005 to about 0.10 wt. % acetamiprid and from about 0.001 to about 0.07 wt/% bifenthrin;
   (b) applying a second pesticide composition different from the first pesticide composition to the treatment area hours after applying the first pesticide and within 24 hours of the application of the first pesticide;
   (c) applying a third pesticide composition to the treatment area days after applying the second pesticide, wherein the application of the third pesticide coincides with the bed bug life cycle and occurs within 14 days from applying the first pesticide; and
   (d) optionally providing at least one additional treatment selected from the group consisting of observing the treatment area; exposing the treatment area to ultraviolet light, vacuuming the treatment area, steaming the treatment area, laundering a treated article, disposing of a treated article, applying a heat or cold treatment to the treatment area, and sealing cracks and crevices in the treatment area.

2. The method of claim 1, wherein the second pesticide composition is selected from the group consisting of a dust, a contact agent, a flushing agent, a liquid residual pesticide, a wetted powder, and combinations thereof.

3. The method of claim 1, wherein the first pesticide is applied to the treatment area at least twice.

4. The method of claim 1, wherein when the first pesticide composition is applied to bed bug eggs, 100% of bed bug eggs remain unhatched two weeks after treatment with the pesticide composition.

5. The method of claim 1, wherein the first pesticide composition consists of:
   (a) acetamiprid;
   (b) bifenthrin; and
   (c) one or more adjuvants selected from the group consisting of a carrier, a surfactant, a pheromone, a food attractant, and combinations thereof;
   wherein when applied to bed bug eggs, 100% of bed bug eggs remain unhatched two weeks after treatment with the pesticide composition.

6. A method of treating or preventing bed bugs, the method comprising:
   (a) inspecting the surface of an article for the presence of bed bugs;
   (b) applying a treatment to the article, wherein the treatment comprises a first pesticide composition selected from the group consisting of an insecticide spray, an insecticide dust, and combinations thereof, wherein the insecticide comprises acetamiprid and bifenthrin;
   (c) encasing the article;
   (d) applying a second pesticide composition to the article hours after and within 24 hours of applying the first pesticide composition; and
   (e) providing at least one additional treatment selected from the group consisting of vacuuming the article, steaming the article, laundering the article, disposing of the article, applying a heat or cold treatment to the article, and sealing cracks and crevices on the article.

7. The method of claim 6, wherein the article is selected from the group consisting of a mattress, a boxspring, bedding, baseboards, headboards, nightstands, carpet, furniture, walls, ceilings, floors, clothing, appliances, pet bedding, and combinations thereof.

8. The method of claim 6, wherein the article is in a location selected from the group consisting of a hotel, a house, a restaurant, an apartment, a movie theater, a train, a bus, an airplane, a car, a truck, a retail store, a college dormitory, a hospital, and a nursing home.

9. The method of claim 6, wherein the treatment is an insecticide spray and wherein the insecticide spray further comprises optional additional adjuvants selected from the group consisting of a carrier, a surfactant, a pheromone, a food attractant, and combinations thereof;
   wherein when applied to bed bug eggs, 100% of bed bug eggs remain unhatched two weeks after treatment with the insecticide spray.

10. A method for treating or preventing bed bugs, the method comprising:
    (a) applying a first pesticide composition to a treatment area;
    (b) applying a second pesticide composition to the treatment area within 24 hours of applying the first pesticide composition; and
    (c) applying a third pesticide composition to the treatment area days after applying the second pesticide and up to 14 days from applying the first pesticide composition, wherein the first pesticide composition consists of acetamiprid, bifenthrin and optional adjuvants selected from the group consisting of a carrier, a surfactant, a pheromone, a food attractant, and combinations thereof.

11. The method of claim 10 wherein the treatment area is a surface of an article, and wherein the method further comprises encasing the article after applying the first pesticide composition.

12. The method of claim 10 further comprising subjecting the treatment area to treatment by UV radiation.

13. The method of claim 10 wherein 100% of bed bug eggs remain unhatched two weeks after treatment with the first pesticide composition.

14. The method of claim 10 wherein the second pesticide composition is the same as the first pesticide composition.

15. The method of claim 1, wherein the third pesticide composition is different from the first pesticide composition.

16. The method of claim 1, wherein the second and third pesticide compositions are the same.

17. The method of claim 1, wherein the first pesticide composition comprises a wetted powder.

* * * * *